United States Patent [19]

Antebi

[11] Patent Number: 4,778,470

[45] Date of Patent: Oct. 18, 1988

[54] WEIGHT DISTRIBUTING PROSTHESIS FOR ABOVE AND BELOW THE KNEE AMPUTATION

[76] Inventor: Eliahu Antebi, 22 Ehud Street, Tel-Aviv, Israel

[21] Appl. No.: 725,237

[22] Filed: Apr. 19, 1985

[30] Foreign Application Priority Data

Apr. 25, 1984 [IL] Israel ........................................ 71638

[51] Int. Cl.⁴ ................................................ A61F 2/28
[52] U.S. Cl. ................................................ 623/16
[58] Field of Search .................. 623/16, 17, 18, 19, 623/20, 21, 22, 23, 10, 11; 128/334 C, 334 R

[56] References Cited

U.S. PATENT DOCUMENTS

| 456,142 | 7/1891 | Garner | 403/199 |
|---|---|---|---|
| 2,896,293 | 7/1959 | Love | 248/523 |
| 3,493,202 | 2/1970 | Jensen | 403/199 |
| 4,158,895 | 6/1979 | Reswick et al. | 623/16 |
| 4,547,912 | 10/1985 | Sherua-Parker | 623/76 |

FOREIGN PATENT DOCUMENTS

| 248474 | 6/1912 | Fed. Rep. of Germany | 403/199 |
|---|---|---|---|
| 603752 | 9/1925 | France | 403/199 |
| 0957894 | 9/1982 | U.S.S.R. | 623/10 |
| 596421 | 1/1948 | United Kingdom | 403/199 |

*Primary Examiner*—Richard J. Apley
*Assistant Examiner*—David J. Isabella
*Attorney, Agent, or Firm*—Benjamin J. Barish

[57] ABSTRACT

A prosthesis made of metal, plastic, or combination, to be installed at the cut edge of the bone during amputation of the limb in order to enlarge the weight-bearing area of the bone at the stump, the said prosthesis including a wide base, provided with a socket or pin, by which it will be attached to the bone.

4 Claims, 3 Drawing Sheets

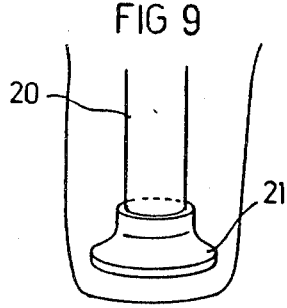
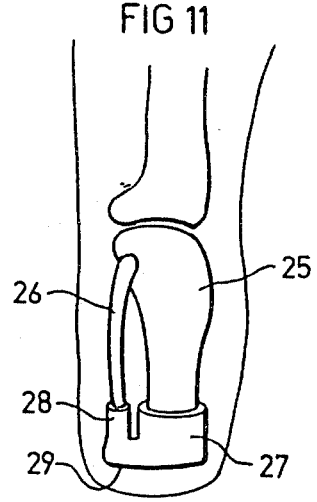
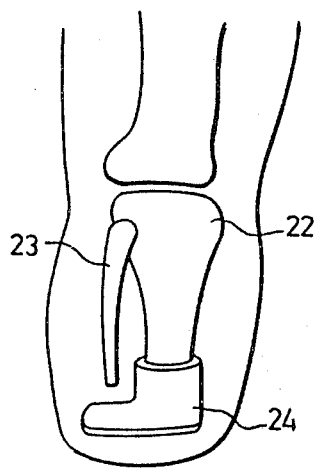
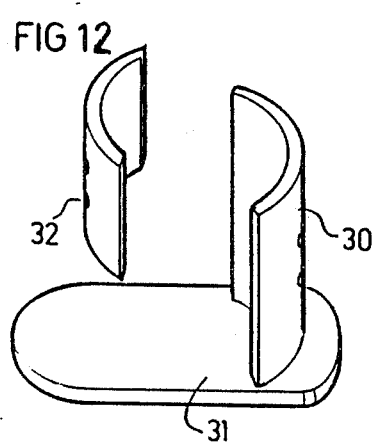
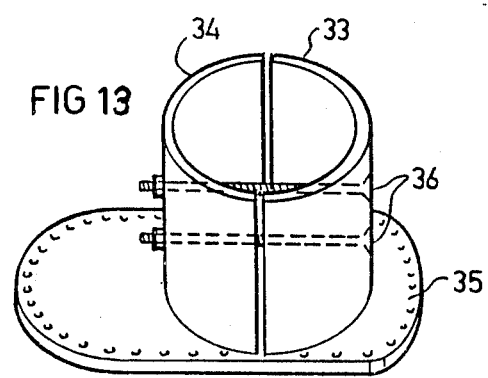

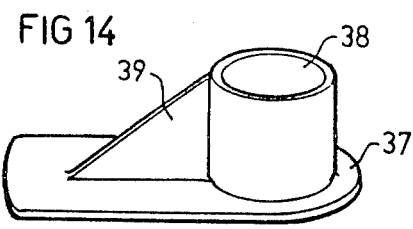
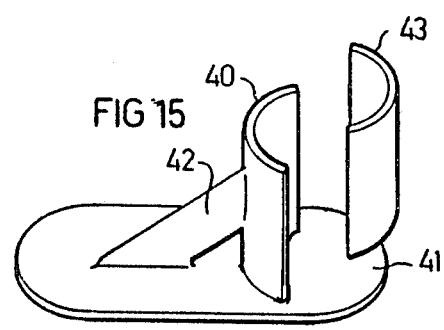
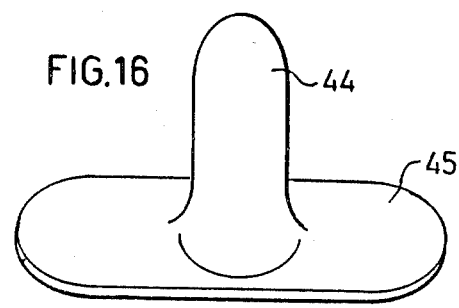
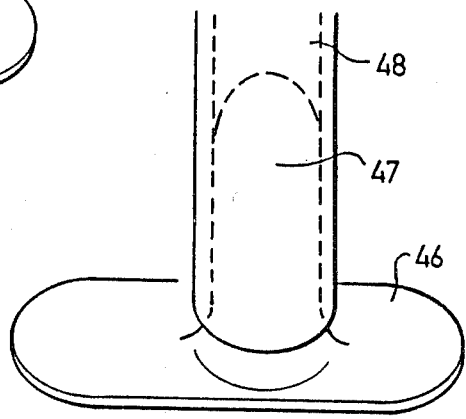
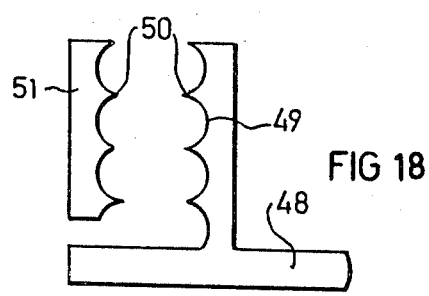

WEIGHT DISTRIBUTING PROSTHESIS FOR ABOVE AND BELOW THE KNEE AMPUTATION

BACKGROUND OF THE INVENTION

The present invention concerns a prosthetic device to be installed during below or above the knee amputations in order to widen the weight bearign area of the bone and enable bearing the body weight on the distal part of the stump.

Amputations are done today on the following indications:
1. After traumatic injury with extensive damage that did not allow for repair.
2. Tumors of the bone, soft tissue, nerves and vascular system.
3. Severe infection with sepsis that critically endangers life and cannot be controlled with antibiotic therapy.
4. Variety of peripheral vascular diseases.

The majority of the amputations done today all over the world concern the last indication (peripheral vascular diseases).

The site of the amputations is decided according to the condition of the tissues and the blood supply, the preference being below the knee amputation if possible. The stump below the knee should be 5" or 6" long in order to enable free movement of the knee joint. The lever is stronger enabling better movement when the stump is longer.

The preferred prosthesis for below the knee amputation is the PTB-Patellar Tendon Bar prosthesis with a total contact socket. The patellar tendon tolerates the major load. The medial flare of the tibia is also utilized for weight bearing.

The preferred prosthesis for above the knee amputation is the Suction Socket Prosthesis in which the prosthesis is held on by suction and close anatomic fit.

In both of the prosthesis the pressure is not put solely on the bone and is distributed over the stump. Direct pressure on the bone is accompanied usually with pain.

The patient who underwent below the knee amputation usually uses the knee for weight bearing rather than step on the stump when moving from place to place without wearing the prosthesis. Stepping on the stump may induce pain and pressure wound can develop on the skin that covers the bone. Protusion of the bone through the skin is a very serious complication. It is thus obvious that an amputee could not transfer the body weight on the bottom of the stump.

In a normal individual the pressure is distributed over almost the whole foot which constitutes a much wider area than the cross section area of the bone through which the weight is transferred.

BRIEF SUMMARY OF THE INVENTION

The new invention is aimed to enlarge the area of the lower end of the bony structure of the stump of an amputee and so distribute the pressure over a larger area.

According to the present invention, there is provided a prosthesis to be attached to the cut bone of a stump following amputation of a limb, comprising: a base of rigid material and of a large cross-sectional area; said base being integrally formed with an attaching element projecting from one face thereof for attaching same to the cut bone; said base being further formed with a plurality of holes around the circumference thereof for suturing thereto body tissue at the stump.

The surface of the base within the circumferential holes and opposite to the attaching element may be smooth, may be formed with a further plurality of holes of larger size than the circumferential holes, or may be formed with ribs of an egg-crate configuration.

Several embodiments of the invention are described below for purposes of example. In some described embodiments, the attaching element is a socket for receiving the cut bone at the stump. In other described embodiments, it is a pin for insertion into the cut bone at the stump.

According to another described feature, the prosthesis may also include a bracing plate integrally formed with the base and the socket; the bracing plate being of a generally triangular configuration, with its base of the same height as the socket and joined thereto along a line extending radially through the socket.

The invention also provides a prosthesis for use in a below-the-knee amputation, comprising a base of rigid material and of a large cross-sectional area; a first socket integrally formed with the base and configured to receive the cut tibia at the amputation; and a second socket integrally formed with the base laterally of the first socket and configured to receive the cut fibula at the amputation.

Further features of the invention will be apparent from the description below.

BRIEF DESCRIPTION OF THE DRAWINGS

The present invention is illustrated by way of example only in the accompanying drawings in which:

FIG. 9 illustrates a prosthesis attached to the femur bone.

FIG. 10 illustrates a prosthesis attached to the tibia.

FIG. 11 illustrates a two bone prosthesis attached to the tibia and fibula after below the knee amputation.

FIG. 12 illustrates a prosthesis which is built from a partially open socket and a plate that will close the socket with screws.

FIG. 13 illustrates the partially open socket prosthesis in the closed position.

FIG. 14 illustrates a ramp shaped support to the one piece socket prosthesis.

FIG. 15 illustrates a ramp shaped support to the divided socket prosthesis.

FIG. 16 illustrates a wide base prosthesis with a pin for intramedulary fixation to the bone.

FIG. 17 illustrates a wide base prosthesis attached to the bone by way of intramedulary fixation.

FIG. 18 illustrates a partially open socket prosthesis where the two parts embracing the bone are not smooth.

DESCRIPTION OF PREFERRED EMBODIMENTS

Figure 1:
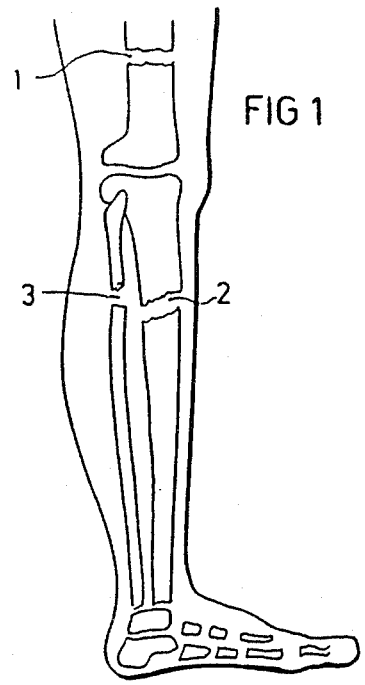
FIG. 1 is a schematic drawing of a leg with the preferred sites of amputation.

The prosthesis is built of a base of rigid material and of a large cross-sectional area provided with an attaching element, for example a socket or a pin by which the base will be attached to the bone. In case of two bones, two sockets can be provided. The device can be built from hard plastic or metal and may be completely smooth at the base.

The device will be secured internally or externally to the bone with screws and if necessary with cement.

The socket to which the bone is introduced is built either as a one-piece socket to fit the bone or as a partially opened socket to be completed with a plate. Securing the bone to the device may be done in this case by screws that may press the bone and the plate to the prosthesis as illustrated in FIG. 13.

The parts of the prosthesis that embraces the bone can be smooth or built with ribs as illustrated in FIG. 18.

The outer surface of the device has holes to which body tissue at the stump, for example muscle tissue or fascia tissue, can be sutured.

The base of the prosthesis may be built in three different ways:
1. completely smooth
2. completely smooth with holes
3. ribbed, like in an egg carton.

The prosthesis and its application is illustrated in the drawings attached.

FIG. Location 1 illustrates a leg with the preferred sites of amputation. 1 is the place for above the knee amputation. The femur is amputated at its lower third. For below the knee amputation location 2 is the preferred site for dividing the tibia. Element 3 is the preferred site for dividing the fibula. The fibula is customarily cut shorter than the tibia.

Figure 2:
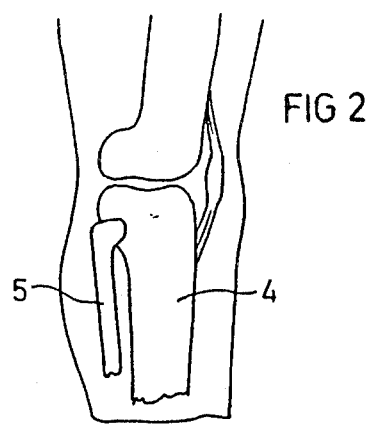
FIG. 2 is a schematic drawing of the stump after below the knee amputation.

FIG. 2 illustrates a stump of below the knee amputation. Element 4 is the cut stump of the tibia. Element 5 is the cut stump at the fibula.

Figure 3:
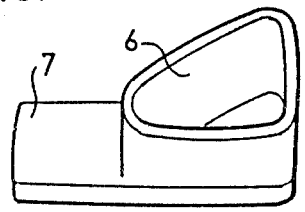
FIG. 3 is an overall view of the prosthesis described in this invention to be attached to one bone only, e.g. the femur or tibia.

FIG. 3 illustrates the prosthesis. Element 6 is the socket to which the cut stump of the femur or tibia is introduced. Element 7 is the wide base on which the pressure will be distributed.

Figure 4:
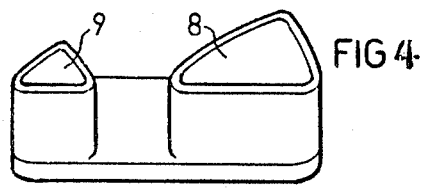
FIG. 4 is an overall view of the prosthesis for two bones; the tibia and fibula.

FIG. 4 is a prosthesis for below the knee amputation. Element 8 is the socket to which the tibia will be introduced. Element 9 is the socket to which the fibula will be introduced. Element 10 is the wide base for distributing the pressure.

Figure 5:
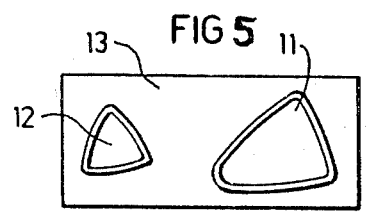
FIG. 5 is an upper view of a two bone prosthesis.

FIG. 5 illustrates the upper view of the prosthesis. Element 11 is the socket to which the tibia is introduced. Element 12 is the socket to which the fibula is introduced. Element 13 is the wide base.

Figure 6:
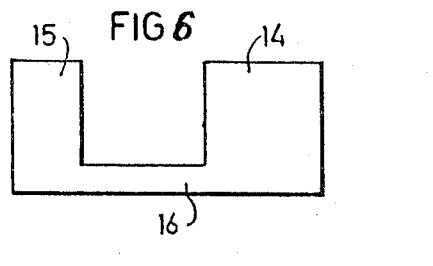
FIG. 6 is a side view of a two bone prosthesis.

FIG. 6 is the side view of the prosthesis. Element 14 is the socket to which the tibia is introduced. Element 15 is the socket to which the fibula is introduced. Element 16 is the broad base.

Figure 7:
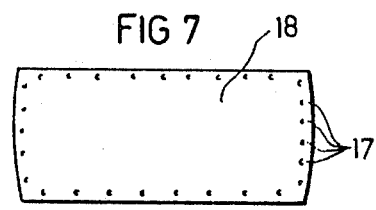
FIG. 7 is the bottom view of a smooth base prosthesis.

FIG. 7 illustrates the bottom view of the prosthesis. Element 17 are the small holes for possible suturing the prosthesis to the muscle or fascia. Element 18 is the smooth wide base.

Figure 8:
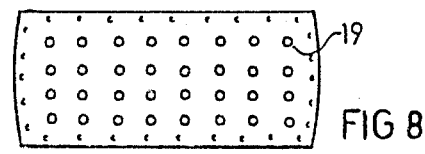
FIG. 8 is the bottom view of a base with many holes in it.

FIG. 8 illustrates a modification wherein the portion of the base within the circumferential holes (17, FIG. 7) is also formed with a plurality of holes but of larger sizes than the circumferential holes.

FIG. 9 illustrates a prosthesis attached to the femur bone after above the knee amputation. Element 20 is the femur bone. Element 21 is the prosthesis.

FIG. 10 illustrates the prosthesis attached to the tibia after below the knee amputation. Element 22 is the stump of the tibia. Element 23 is the stump of the fibula. Element 24 is the prosthesis attached to the tibia alone.

FIG. 11 illustrates the prosthesis attached to the tibia and fibula where Element 25 is the stump of the tibia, and Element 26 is the stump of the fibula. Element 27 is the socket for the tibia. Element 28 is the socket for the fibula. Element 29 is the wide base to which the body weight will be delivered.

FIG. 12 illustrates the divided prosthesis. Element 30 is part of the socket that is built as one piece with the base 31. Element 32 illustrates the plate that will close the socket and will embrace the bone.

FIG. 13 illustrates the divided socket prosthesis in the closed position. Element 33 illustrates the part of the socket which is built with the base 35. Element 34 illustrates the plate that completes the socket and shown at 36 are the screws that close the socket.

FIG. 14 illustrates a construction including a base 37 integrally formed with a one-piece socket 38 and also including a bracing plate 39 integrally formed with the base and the socket. Bracing plate 39 is of generally triangular configuration and is joined to the socket along a line extending radially with respect to the socket.

FIG. 15 illustrates a prosthesis including a base 41 formed with a split socket having a first section 40 integrally formed with the base, and a second section 43 attachable to section 40 by the use of fasteners (not shown) as illustrated in FIGS. 12 and 13 respectively. The prosthesis illustrated in FIG. 15 further includes a ramp or bracing plate 42 similar to that illustrated with respect to FIG. 14 integrally formed with base 41 and section 40 of the socket.

FIG. 16 illustrates a wide base prosthesis wherein the attaching element is in the form of a pin 44 integrally formed with the wide base 45 and to be inserted into the bone intramedularly.

FIG. 17 illustrates a prosthesis with a wide base—46— —and a pin—47—attached intramedularly to the cut edge of the bone.

FIG. 18 illustrates a sagital section of an open socket prosthesis. This prosthesis also includes a split-socket construction including a wide base 48 integrally formed with one socket section 49. A second socket section 51 is attachable to section 49 by fasteners (not shown) passing through both sections and the bone received between them, as described above with respect to FIGS. 12 and 13. In the example illustrated in FIG. 18, however, the inner faces of the two socket sections 49 and 51 are not smooth and substantially semi-cylindrical, as in FIGS. 12 and 13, but rather are formed with ribs 50 for firmly grasping the bone received between them.

It will be appreciated that the examples illustrated in FIGS. 16–18 would also include the holes corresponding to holes 17 in FIG. 7, formed around the circumference of the respective base plate for suturing thereto body tissue, such as muscle tissue or fascia tissue, at the stump.

I claim:

1. An implantable prosthesis to be attached to a stump of an amputated bone in order to widen the weight bearing area of the bone, said prosthesis comprising a wide base of rigid material, said base having a cross-sectional area much wider than the cross-sectional area of the amputated bone, said base being integrally formed with a substantially cylindrical socket projecting from one face thereof for attaching said prosthesis to said stump, said socket formed of two pieces such that each piece is attached to opposite sides of the outer surface of the bone and each piece having holes therein for receiving fastening means which pass through said holes of one piece through said bone and into said holes of opposite piece thereby clamping said prosthesis to the bone.

2. The implantable prosthesis according to claim 1, wherein said prosthesis further includes a bracing plate integrally formed with said base and said socket; said bracing plate being of a generally triangular configuration and joined to the socket along a line extending radially with respect to the socket.

3. The prosthesis according to claim 1, wherein each of said sections is formed with a substantially semi-cylinderical inner face.

4. The prosthesis according to claim 1, wherein each of said sections is formed with a ribbed inner face.

* * * * *